United States Patent [19]

Imai

[11] 4,357,479

[45] Nov. 2, 1982

[54] PRODUCTION OF ALCOHOLS

[75] Inventor: Tamotsu Imai, Mount Prospect, Ill.

[73] Assignee: UOP Inc., Des Plaines, Ill.

[21] Appl. No.: 308,705

[22] Filed: Oct. 5, 1981

Related U.S. Application Data

[63] Continuation-in-part of Ser. No. 134,032, Mar. 26, 1980, abandoned.

[51] Int. Cl.$^3$ ............................................. C07C 29/04
[52] U.S. Cl. .................................................. 568/899
[58] Field of Search ........................................ 568/899

[56] References Cited

U.S. PATENT DOCUMENTS

| | | | |
|---|---|---|---|
| 2,014,740 | 9/1935 | Larson | 260/156 |
| 2,057,283 | 10/1936 | van Peski et al. | 260/156 |
| 2,126,952 | 8/1938 | Dreyfus | 260/614 |
| 2,162,913 | 6/1939 | Eversole et al. | 260/641 |
| 2,756,247 | 7/1956 | James, Jr. et al. | 260/449 |
| 2,961,472 | 11/1960 | Welch et al. | 260/677 |

FOREIGN PATENT DOCUMENTS

| | | |
|---|---|---|
| 408006 | 3/1934 | United Kingdom . |
| 748959 | 5/1956 | United Kingdom . |

*Primary Examiner*—Joseph E. Evans
*Attorney, Agent, or Firm*—James R. Hoatson, Jr.; Raymond H. Nelson; William H. Page, II

[57] ABSTRACT

The production of alcohols in which an olefinic hydrocarbon is hydrated with a liquid water in the presence of an aqueous sulfur-containing acid catalyst such as sulfuric acid may be improved by effecting the reaction in the presence of a solid, porous carbon support which will act as the co-catalyst or promoter. The hydration reactions which are employed for the process will include a temperature in the range of from about 100° to about 300° C. and a pressure in the range of from about 1 to about 300 atmospheres.

10 Claims, No Drawings

PRODUCTION OF ALCOHOLS

CROSS-REFERENCE TO RELATED APPLICATION

This application is a continuation-in-part of my copending application Ser. No. 134,032, filed Mar. 26, 1980, now abandoned, all teachings of which are incorporated herein.

BACKGROUND OF THE INVENTION

The preparation of alcohols from various sources is known in the art. For example, U.S. Pat. No. 2,162,913 discloses a process for hydrating olefins in the presence of heteropoly acids. The patent teaches that an inert porous support such as alumina may be used as a carrier for heteropoly acids such as organic complexes of high molecular weight in which the nuclear element such as phosphorus, silica, boron, or arsenic is surrounded by a coordinated group of other metallic oxide or oxides such as the oxides of tungsten, molybdenum, vanadium, chromium, sulfur, selenium or tellurium. This heteropoly acid-supported catalyst is heterogeneous in nature and is not homogeneous. U.S. Pat. No. 2,014,740 discloses the hydration of olefins with steam in a vapor phase process as does U.S. Pat. No. 2,057,283. The catalysts which are employed for these reactions comprise, in the former case, a solution of a volatile halide such as ammonium chloride, hydrogen chloride, hydrogen bromide, methyl chloride, ethyl iodide, etc. over an adsorbent material such as pumice, silica gel, coke and the like, while the latter patent uses a metal compound which does not yield the metal under reaction conditions in a finely divided state or on a suitable carrier which may include the types used in the former patent. In a similar manner, U.S. Pat. No. 2,126,952 and British Patent No. 748,959 teach the production of alcohols in which an olefin is hydrated in the gaseous or vapor phase. The U.S. patent uses, as a catalyst for the reaction, a bisulfate or pyrosulfate of the alkali metals and chlorides such as calcium chloride, zinc chloride and manganese chloride. The reaction in the vapor phase may also contain a filling material or carrier such as pumice, kieselguhr, carborundum or silica gel. The British patent specification utilizes a phosphoric acid on a porous carrier for the catalyst.

U.S. Pat. No. 2,756,247 relates to a process for chemical reaction in the adsorbed phase of solid adsorbents, said process consisting of adsorbing an olefin on an activated charcoal-supported catalyst followed by the hydration and stripping of the adsorbed olefin with steam and the secondary stripping of adsorbed alcohol with steam. The hydration of the olefin is effected in a vapor phase and care is taken during the operation to prevent the condensation of the outer surfaces of the support. British Pat. No. 408,006 teaches the hydration of gaseous ethylene and steam utilizing, as a catalyst therefor, sulfuric acid, phosphoric acid or mixtures thereof. In order to increase the efficiency of gas distribution, a filling material may be utilized in order to promote the contact of the gas and acid. The filling material which is utilized for this purpose may comprise carriers such as pumice, silica gel, etc., all of which possess a low surface area.

Another U.S. patent, namely U.S. Pat. No. 2,961,472 relates to the hydration of an olefin using vacuum reconcentrated sulfuric acid. The reconcentrated sulfuric acid which is utilized in this process must contain less than 0.2% by weight, and preferably less than 1.0% by weight, of normal non-aqueous deleterious impurities and cites, as an example of these impurities, carbon. This patent therefore teaches that the presence of an impurity such as carbon in an amount greater than 2.0% by weight would be disadvantageous to the operation of a reaction involving an olefin.

As will hereinafter be shown in greater detail, it has now been discovered that alcohols may be produced from olefins by treatment with liquid water in the presence of an acid catalyst such as aqueous sulfuric acid utilizing a solid porous material as a co-catalyst.

BRIEF SUMMARY OF THE INVENTION

This invention relates to a process for the production of alcohols. More specifically, the invention is concerned with a process for the production of alcohols in which the catalytic activity of acid catalysts which are employed to effect the reaction may be improved by the presence of a co-catalyst of a type hereinafter set forth in greater detail.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, beverages, etc. Isopropyl alcohol is used in the manufacture of acetone which, in turn, is a source of acetic anhydride, diacetone alcohol, methyl isobutyl ketone and other derivatives. It is also used as a solvent for essential oils, gums, resins; as a latent solvent for cellulose derivatives; as an anti-stalling agent in liquid fuels or as an intermediate in the manufacture of pharmaceuticals, perfumes, lacquers, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, antifoam agent, as a perfume fixitive for soaps and cosmetics as well as other uses.

The prior art is replete with processes for the production of alcohols from olefinic hydrocarbons utilizing various organic and inorganic acids as catalyts for the reaction. However, it has now been discovered that the catalytic activity of these acids may be improved, especially in the area of olefin conversion, by utilizing a solid porous substrate, of either organic or inorganic composition, as a co-catalyst in the reaction mixture.

It is therefore an object of this invention to provide an improved process for the production of alcohols.

A further object of this invention is to provide an improved catalyst system for producing alcohols from olefinic hydrocarbons.

In one aspect, an embodiment of this invention resides in a process for the production of an alcohol in a vapor-liquid mixed phase environment which comprises hydrating a vaporous olefinic hydrocarbon containing from 2 to about 30 carbon atoms with liquid water at hydration conditions which include a temperature in the range of from about 100° to about 300° C. and a pressure in the range of from about 1 to about 300 atmospheres, wherein said hydration conditions are selected to insure that said water remains in a liquid phase in the presence of a liquid sulfur-containing acid catalyst and a co-catalyst consisting essentially of a solid, porous, hydrophobic or hydrophilic carbon and recovering the resultant alcohol.

A specific embodiment of this invention is found in a process for the production of an alcohol which comprises hydrating propylene with water in the presence of a catalyst system comprising sulfuric acid and activated carbon at a temperature in the range of from about 100° to about 300° C. and a pressure in the range of from about 1 to about 300 atmospheres, and recovering the resultant isopropanol.

Other objects and embodiments will be found in the following further detailed description of the present invention.

DETAILED DESCRIPTION OF THE INVENTION

As hereinbefore set forth, the present invention is concerned with an improvement in a process for the production of alcohols in which olefinic hydrocarbons are subjected to a hydration reaction in the presence of an acid catalyst such as sulfuric acid which is in the form of an aqueous solution, the improvement is afforded by the presence of a solid, porous material which is present as a co-catalyst. The co-catalyst which may also be referred to as a promoter accelerates the hydration reaction by means of a mechanism in which the concentrations of an acid catalyst, water and an olefin are increased on the surface of the co-catalyst due to the fact that the compounds are adsorbed on the co-catalyst. The reaction of the adsorbed species increases in comparison with other former reactions utilizing a homogeneous catalytic reaction, inasmuch as the concentrations of reactants and catalyst are higher with a concurrent lower activation energy for the reaction due to the aforementioned adsorption of the various components of the reaction. In addition, the hydration reaction is effected in a vapor-liquid mixed phase environment. The conditions which are employed to effect the desired reaction will include elevated temperatures in the range of from about 100° to about 300° C. or more and pressures within a range of from about 1 to about 300 atmospheres, the particular hydration conditions which are used being those which are selected to insure that the water which is used for the hydration will remain in a liquid phase. It is contemplated that the superatmospheric pressures which are employed will be afforded by the autogenous pressure of the olefinic hydrocarbon, if in gaseous form, or by the introduction of a substantially inert gas such as nitrogen, helium, argon, etc. into the reaction zone. In addition to the aforementioned hydration conditions of temperature and pressure, another operating parameter of the present reaction is that the water which is utilized to hydrate the olefinic hydrocarbon is present in a mole ratio of from about 2:1 up to about 60:1 moles of water per mole of olefin.

Examples of olefinic hydrocarbons which may be employed as the starting materials in the process of this invention will comprise olefins containing from 2 to about 20 carbon atoms or more, and preferably those containing from 2 to 4 carbon atoms. Specific examples of these olefinic hydrocarbons will include ethylene, propylene, butene-1, butene-2, isobutylene, pentene-1, pentene-2, hexene-1, hexene-2, hexene-3, as well as the isomeric, both straight and branched chain, heptenes, octenes, nonenes, decenes, hendecenes, dodecenes, tridecenes, tetradecenes, pentadecenes, hexadecenes, heptadecenes, octadecenes, nonadecenes, eicosenes, etc. Acidic catalysts which are employed to effect the reaction of the present invention will comprise an aqueous sulfur-containing acid such as sulfuric acid, benzenesulfonic acid, toluenesulfonic acid, trifluoromethanesulfonic acid, etc. in which the sulfur-containing acid portion of the compound may be present in a range of from about 1% to about 50% by weight of the solution. It is also contemplated within the scope of this invention that other aqueous solutions of acids, such as hydrochloric acid, nitric acid, phosphoric acid, heteropoly inorganic acids such as 12-tungstosilicic acid, 12-tungstophosphoric acid, 12-tungstogermanic acid, 10-tungsto-2-vanadophosphoric acid, 12-molybdophosphoric acid, etc. may also be employed, although not necessarily with equivalent results.

As hereinbefore set forth, it has now been discovered that the catalytic activity of the aforementioned sulfur-containing acid catalysts may be increased by employing a solid, porous material as a co-catalyst or promoter. In the preferred embodiment of the invention, the solid, porous material will include carbon substrates such as activated carbon or carbon which possesses large size pores and which may be either hydrophilic or hydrophobic in nature. The carbon in activated form may be activated by any means known in the art, or the porous carbons which possess large pore size may be prepared by depositing the carbon or a carbonaceous material on an inorganic oxide such as alumina and thereafter dissolving the inorganic oxide by leaching with a mineral acid, thus leaving the carbon structure which possesses the desirable pore size. The solid, porous substrate which acts as a co-catalyst or promoter will be present in the catalyst system in an amount in the range of from about 0.05 to 30 volumetric ratio of the co-catalyst to an aqueous acid catalyst, and preferably in a ratio of from about 1 to about 20.

The process of the present invention may be effected in any suitable manner and may comprise either a batch or continuous type operation. For example, when a batch type of operation is employed, the desired quantity of water is placed in an appropriate pressure resistant apparatus such as an autoclave of the rotating, mixing or stirring type along with the aqueous acid catalyst and the desired solid porous substrate of the type hereinbefore set forth in greater detail. The apparatus is sealed and the olefinic hydrocarbon, if in gaseous form, is pressed in until the desired operating pressure has been attained. Thereafter, the vessel and contents thereof are heated to the desired operating temperature and maintained thereat for a predetermined period of time which may range from about 0.5 up to about 10 hours or more in duration, the residence time being dependent upon the operating parameters of temperature and pressure as well as the olefinic hydrocarbon which is to undergo hydration. In the event that the olefinic hydrocarbon is in liquid form, it is also charged to the reactor prior to sealing the vessel. After charging the olefinic hydrocarbon to the vessel and sealing the same, the desired operating pressure is attained by charging an inert gas thereto. Upon completion of the reaction, heating is discontinued and after the vessel and contents thereof have returned to room temperature, the excess pressure is discharged and the vessel is opened. The reaction mixture is recovered from the vessel and subjected to conventional means of separation such as fractional distillation, fractional crystallization, etc. whereby the desired alcohol is separated from the catalyst, water, substrate and any unreacted olefinic hydrocarbon.

It is also contemplated within the scope of this invention that a continuous manner of operation may be employed to produce the desired product. When such a type of operation is used, the olefinic hydrocarbon comprising the feedstock is continuously charged to a reaction vessel which contains the acid catalyst, water and solid porous co-catalyst. After passage through the vessel, which is maintained at the proper operating conditions of temperature and pressure, the reactor effluent is continuously withdrawn and subjected to conventional means of separation whereby the desired alcohol is recovered while any unreacted olefin, water or aqueous catalyst are recycled to the reaction zone to form a portion of the feedstock.

The following examples are given to illustrate the process of this invention. However, it is to be understood that these examples are merely illustrative of the process of this invention and that this process is not merely limited thereto.

EXAMPLE I

In this example, 10.86 grams of sulfuric acid and 200.6 grams of water were placed in a rotating autoclave along with 9.05 grams of a hydrophilic carbon sold under the tradename Pittsburgh CPG by the Pittsburgh Activated Carbon Company. The autoclave was sealed and 25.69 grams of a propylene-propane blend consisting of 65% propylene and 35% propane was charged to the autoclave. The autoclave was then heated to a temperature of 174° C. and maintained thereat for a period of 1 hour. The original operating pressure of 30 atmospheres dropped to 29 atmospheres during this period. At the end of the 1 hour period, heating was discontinued and after the autoclave had returned to room temperature, the excess pressure was discharged and the autoclave was opened. The reaction mixture was recovered and subjected to gas chromatographic analysis. This analysis disclosed that there had been a 51.1% conversion of the propylene with a 98.7% selectivity to isopropyl alcohol, the remaining 1.3% being diisopropyl ether.

EXAMPLE II

In a manner similar to that set forth in Example I above, 10.85 grams of sulfuric acid, 200 grams of water and 9.8 grams of a hydrophobic carbon sold under the trade name Witco 940 by the Witco Company was placed in an 850 cc rotating autoclave. The autoclave was sealed and 26.02 grams of a $C_3$ blend consisting of 65% propylene and 35% propane was charged thereto. The autoclave was then heated to a temperature of 174° C. and maintained thereat for a period of 1 hour, the pressure during this reaction period being about 31 atmospheres. At the end of the 1 hour period, heating was discontinued, the excess pressure was discharged and the autoclave was opened. The reaction mixture was then subjected to gas chromatographic analysis which disclosed a 53.8% conversion of propylene with a product selectivity consisting of 98.5% isopropyl alcohol and 1.5% diisopropyl ether.

When the above experiment was repeated using 10.6 grams of sulfuric acid, 400.4 grams of water and 10.1 grams of Witco 940 carbon, the percent of sulfuric acid in the water being 2.5 and the mole ratio of water to propylene being 59:1, it was determined that there had been a 58.9% conversion of the propylene with a 97.9% selectivity to isopropyl alcohol and 2.1% to diisopropyl ether.

EXAMPLE III

In a manner similar to that set forth in the above examples, 10.57 grams of sulfuric acid, 200.25 grams of water and 8.34 grams of a hydrophobic carbon sold under the trade name Columbia LXC by the Union Carbide Corporation were placed in an 850 cc rotating autoclave. The autoclave was sealed and 24.83 grams of a propylene-propane blend gas of similar makeup to that attained in the above experiment was charged to the reactor. The reactor was then heated to a temperature of 170° C. with an initial operating pressure of about 34 atmospheres. During the 1 hour residence time, the temperature dropped from 170° to 165° C. It is to be noted in this experiment that the mole ratio of water to propylene was 30:1. At the end of the 1 hour period, heating was discontinued, the autoclave was allowed to return to room temperature and the excess pressure was discharged. The autoclave was opened and after the reaction mixture was recovered it was subjected to gas chromatographic analysis. This analysis showed that there had been a 53.2% conversion of propylene with a 96.6% selectivity to isopropyl alcohol and 3.4% to diisopropyl ether.

EXAMPLE IV

In this example, 25.0 grams of a propylene-propane blend was charged to a reactor which contained 10.73 grams of sulfuric acid, 200.7 grams of water and 9.92 grams of a hydrophilic carbon sold under the trade name Norit PKDA by the Norit Company at a temperature of 174° C. and an operating pressure of about 32 atmospheres for a period of 1 hour. Analysis of the reaction mixture disclosed a 51.8% conversion of the propylene with a 98.2% selectivity to isopropyl alcohol and a 1.8% selectivity to diisopropyl ether.

EXAMPLE V

To illustrate the increase in catalytic activity when using a solid porous substrate as a co-catalyst, another experiment was performed in which 10.7 grams of sulfuric acid and 200.4 grams of water were placed in a rotating autoclave. The autoclave was sealed and 24.7 grams of a propylene-propane blend gas consisting of 65% propylene and 35% propane was charged thereto. It is to be noted that the percentage of sulfuric acid in the water was 5% and there was a mole ratio of water to propylene of 30:1. The autoclave was heated to a temperature of 173° C. with an initial operating pressure of 29 atmospheres. At the end of a 1 hour period, during which time the operating temperature dropped to 170° C., heating was discontinued and after the autoclave had returned to room temperature the excess pressure was discharged. The autoclave was opened and the reaction mixture subjected to gas chromatographic analysis. This analysis disclosed that there had been only a 43.3% conversion of the propylene with a 100% selectivity to isopropyl alcohol.

It is readily apparent, therefore, that by utilizing a solid porous support as a co-catalyst, it is possible to attain an increase in catalytic activity based on the conversion of the olefinic hydrocarbon.

EXAMPLE VI

The use of other acidic catalysts such as benzenesulfonic acid or trifluoromethanesulfonic acid in conjunction with other solid porous supports such as silica, polystyrene, and polytetrafluoroethylene in the hydration of other olefins such as ethylene and butene under reaction conditions similar to those hereinbefore set forth may result in the conversion of said olefins to alcohols such as ethyl alcohol and sec-butyl alcohol at a relatively high rate and selectivity.

I claim as my invention:

1. A process for the production of an alcohol in a vaporliquid mixed phase environment which comprises hydrating a vaporous olefinc hydrocarbon containing from 2 to 4 carbon atoms with liquid water at hydration conditions which include a temperature in the range of from about 100° to about 300° C. and a pressure in the range of from about 1 to about 300 atmospheres, wherein said hydration conditions are selected to insure that said water remains in a liquid phase in the presence of a liquid sulfur-containing acid catalyst and a cocatalyst consisting essentially of a solid, porous, hydrophobic or hydrophilic carbon and recovering the resultant alcohol.

2. The process as set forth in claim 1 in which said carbon is hydrophilic carbon.

3. The process as set forth in claim 1 in which said carbon is hydrophobic carbon.

4. The process as set forth in claim 1 in which said carbon is activated carbon.

5. The process as set forth in claim 1 in which said sulfur-containing acid catalyst is sulfuric acid.

6. The process as set forth in claim 1 in which said sulfur-containing acid catalyst is trifluoromethanesulfonic acid.

7. The process as set forth in claim 1 in which said olefinic hydrocarbon is propylene and said alcohol is isopropyl alcohol.

8. The process as set forth in claim 1 in which said olefinic hydrocarbon is ethylene and said alcohol is ethyl alcohol.

9. The process as set forth in claim 1 in which said olefinic hydrocarbon is butene and said alcohol is sec-butyl alcohol.

10. The process as set forth in claim 1 in which said olefinic hydrocarbon is isobutylene and said alcohol is tert-butyl alcohol.

* * * * *